United States Patent [19]

Witzel

[11] Patent Number: 4,798,823

[45] Date of Patent: Jan. 17, 1989

[54] NEW CYCLOSPORIN ANALOGS WITH MODIFIED "C-9 AMINO ACIDS"

[75] Inventor: Bruce E. Witzel, Westfield, N.J.

[73] Assignee: Merck & Co., Inc., Rahway, N.J.

[21] Appl. No.: 57,196

[22] Filed: Jun. 3, 1987

[51] Int. Cl.⁴ ............... A61K 37/02; C07K 5/12
[52] U.S. Cl. .................................. 514/11; 530/317
[58] Field of Search .................... 530/321; 514/11

[56] References Cited

U.S. PATENT DOCUMENTS

| | | | |
|---|---|---|---|
| 4,108,985 | 8/1978 | Rüegger et al. | 530/321 |
| 4,117,118 | 9/1978 | Harri et al. | 514/11 |
| 4,210,581 | 7/1980 | Rüegger et al. | 530/321 |
| 4,220,641 | 9/1980 | Traber et al. | 514/11 |
| 4,288,431 | 9/1981 | Traber et al. | 530/321 |
| 4,289,851 | 9/1981 | Traber et al. | 530/321 |
| 4,384,996 | 5/1983 | Bollinger et al. | 530/321 |
| 4,396,542 | 8/1983 | Wenger | 530/321 |
| 4,639,434 | 1/1987 | Wenger | 530/321 |
| 4,703,033 | 10/1987 | Seebach | 530/321 |

OTHER PUBLICATIONS

R. Wenger, Sandorama, 1984/111, pp. 5–11.
H. Kobel and R. Traber, European J. Appln. Microbiol. Biotechnol., 14, 237–240 (1982).

Primary Examiner—Delbert R. Phillips
Attorney, Agent, or Firm—Joseph F. DiPrima; Michael C. Sudol; Mario A. Monaco

[57] ABSTRACT

New cyclosporin analogs with modified "C-9 amino acids" have been made and are found to be effective immunosuppressive agents.

19 Claims, No Drawings

NEW CYCLOSPORIN ANALOGS WITH MODIFIED "C-9 AMINO ACIDS"

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Crohns disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

The cyclosporins are a family of immunospressive compounds isolated from fermentation broths of various fungal species including *Tolypocladium inflatum* and *Cylindrocarpon lucidum*.

The generic structure of the class of cyclosporins has been established as a cyclic peptide of formula (I) which contains 11 amino acids.

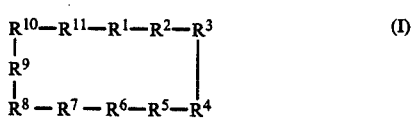

(I)

For example, cyclosporin A of formula (II) contains several N-methylated amino acids and one novel amino acid "MeBMT" designated as the 1- "C-9 amino acid". This novel amino acid is located in position 1 and has been found to be important for the biological activity of cyclosporin. We have found that replacing the double bond of the "C-9 amino acid" (MeBMT) with a hetero atom such as S and O decreases the toxicity of the parent cyclosporin. Substantial activity in the various assays in which cyclosporin A expresses immunosuppressive activity is also exhibited.

STRUCTURE OF CYCLOSPORIN A

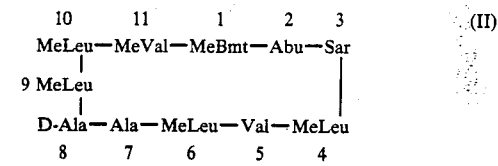

Bmt=(4R)-4-[(E)-2-butenyl]-4-methyl-L-threonine
Me=Methyl
Abu=α-Aminobutyric acid
Val=Valine
Ala=Alanine
MeLeu=N-methyl Leucine
MeVal=N-Methyl valine
Sar=Sarcosine Generally a cyclosporin such as cyclosporin A is not cytotoxic nor myelotoxic. It does not inhibit migration of monocytes nor does it inhibit granulocytes and macrophage action. Its action is specific and leaves most established immune responses intact. However, it is nephrotoxic and is known to cause the following undesirable side effects:

(1) abnormal liver function;
(2) hirsutism;
(3) gum hypertrophy;
(4) tremor;
(5) neurotoxicity;
(6) hyperaesthesia; and
(7) gastrointestinal discomfort.

Accordingly, an object of the present invention is to provide new cyclosporin analogs which will (1) restore the balance of the help-and-suppression mechanism of the immune system by acting at an earlier point than the anti-inflammatory agents and (2) induce specific long-term transplantation tolerance through a suppressor cell circuit without increasing the body's susceptibility to infection.

Another object of the present invention is to provide pharmaceutical compositions for administering to a patient in need of the treatment one or more of the active immunosuppressive agents of the present invention.

Still a further object of this invention is to provide a method of controlling graft rejection, autoimmune and chronic inflammatory diseases by administering a sufficient amount of one or more of the novel immunosuppressive agents in a mammalian species in need of such treatment.

Finally, it is the object of this invention to provide processes for the preparation of the active compounds of the present invention.

DETAILED DESCRIPTION OF THE INVENTION

A. Scope of the Invention

This invention relates to cyclosporins of formula (I)

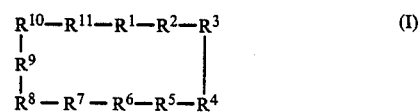

(I)

wherein $R^1$ is 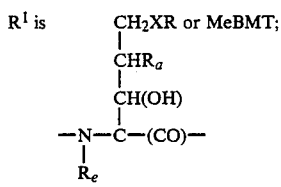

where X, R, $R_a$, and $R_e$ are as defined below;

$R^2$ is L-2-aminobutyryl; norvalyl; L-threonyl; or $R^1$;

$R^3$ is sarcosyl or α-(methylmercapto)sarcosyl; N-methyl-D-alanyl or N-methyl-L-alanyl; or D-prolyl;

$R^4$ is N-methyl-L-leucyl;

$R^5$ is L-valyl; or norvalyl;

$R^6$ is N-methyl-L-leucyl;

$R^7$ is L-alanyl; L-2-aminobutyryl; or L-phenylalanyl;

$R^8$ is D-alanyl or L-alanyl;

$R^9$ is N-methyl-L-leucyl; or N-methyl-L-valyl;

$R^{10}$ is N-methyl-L-leucyl; or L-leucyl;

$R^{11}$ is N-methyl-L-valyl; L-valyl; or L-2-aminobutyryl;

Preferably, this invention relates to a cyclosporin A derivative having modified 1-"C-9 amino acid":

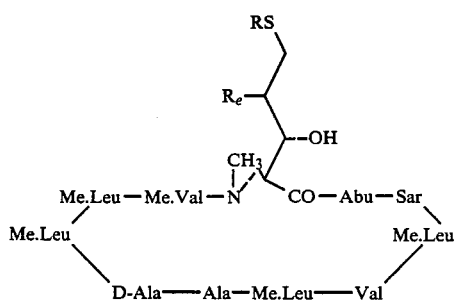

wherein

R is (1) hydrogen;

(2) loweralkyl especially $C_{1-6}$ alkyl such as methyl, ethyl, propyl, isopropyl, t-butyl, pentyl, benzyl, cyclopropyl, cyclopentyl or cyclohexyl;

(3) loweralkenyl especially $C_{2-6}$ alkenyl, for example, vinyl, allyl, and buten-2-yl;

(4) haloloweralkyl especially $C_{1-6}$ haloalkyl such as trifluoromethyl;

(5) aryl especially phenyl or substituted phenyl;

(6) oxyloweralkyl especially alkoxy $C_{1-6}$ alkyl such as —$CH_2OR_b$ where $R_b$ is H or $C_{1-6}$ alkyl;

(7) thioloweralkyl especially alkylthio $C_{1-6}$ alkyl such as —$CH_2SR_a$ wherein $R_a$ is $C_{1-6}$ alkyl; or mercapto $C_{1-6}$ alkyl;

(8) heteroaryl especially pyridyl, pyrryl, furyl or thienyl;

the aryl or heteroaryl group above can be substituted with one or more functional groups e.g., (a) $C_{1-6}$ alkyl, (b) $C_{1-6}$ alkanoyl;

(c) $C_{1-6}$ haloalkyl;

(d) halo;

(e) cyano;

(f) hydroxy $C_{1-3}$ alkyl;

(g) $C_{1-6}$ alkoxy;

(h)

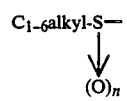

where n is 0, 1 or 2;

(i) —$NR_bCOR_c$ wherein $R_b$ and $R_c$ independently are H or $C_{1-6}$ alkyl;

(j) —$NO_2$;

(k) —$NR_bR_d$;

(l) —$OR_b$;

(m) —$CONR_bR_c$ (n) —$COR_b$;

(o) —$NR_bCONR_bR_c$;

(p) —$NR_bCOR_c$;

(q) —$OCOR_b$;

(r) —$SCOR_b$; or (s) —$OCH_2O$—;

$R_a$ is loweralkyl;

$R_e$ is loweralkyl; loweralkylphenyl especially benzyl or aryl especially phenyl; and X is S, SO, $SO_2$, O, or $NR_b$.

In a more preferred embodiment of this invention,

R is (1) hydrogen;

(2) $C_{1-6}$ alkyl;

(3) —$CF_3$;

(4) phenyl;

(5) $CH_2OR_b$; or (6) $CH_2SR_b$;

$R_a$ is $CH_3$;

X is S or O.

In a even more preferred embodiment of this invention,

R is $C_{1-6}$ alkyl or phenyl;

$R_a$ is $CH_3$; and

X is S.

B. Preparation of the compounds within the scope of the present invention

The cyclosporins of this invention are prepared via cyclization of appropriate linear undecapeptide following well-established procedures which were slightly modified for better results. The procedure most used is published by R. W. Wenger et al. in *Helv. Chim. Acta*, 67, 502(1984). The following scheme illustrates the application of this procedure to the cyclosporins of this invention.

SCHEME I

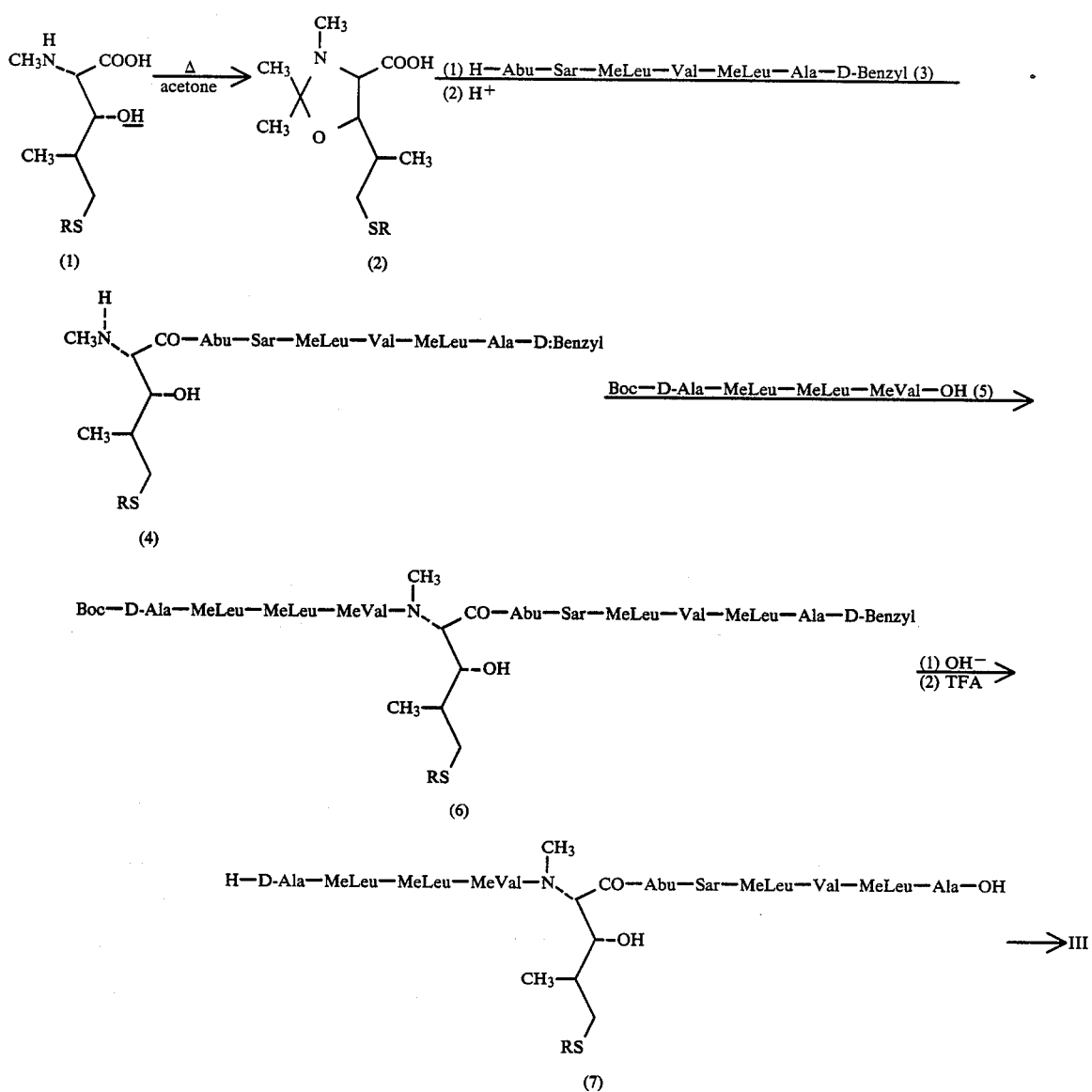

According to the scheme, the threonine derivatives of formula (1) were converted to various cyclic undecapeptides of formula (8) utilizing, for the most part, published procedures. Notably, the methods described in *Helv. Chim. Acta.* 67, 502 (1984) are the preferred procedures.

Generally, the key starting material, (1) was heated in acetone to form the intermediate oxazolidinecarboxylic acid (2). Condensation of compound (2) with the hexapeptide ester (3) in the presence of DCC, N-hydroxybenzotriazole and N-methylmorpholine yielded an intermediate which upon treatment with an acid, for example, HCl in methanol afforded the heptapeptide (4). Further condensation with the tetrapeptide (5) followed by treatment with a strong base (e.g. NaOH or KOH) and then an acid such as TFA yielded the linear undecapeptide (7). Cyclization of compound (7) at high dilution and in the presence of a condensation agent such as 1-propanephosphonic acid cyclic anhydride and dimethylaminopyridine led to the cyclosporin derivative, (8).

Table I below lists the representative compounds prepared by following essentially the same procedures described in Scheme I.

Alternatively, cyclosporins of this invention may be made from existing analogs. For example, treatment of cyclo[[](((2S,3R,[4R]4S)-N,4-dimethyl-4-(methylthiomethyl)-threonyl)-L-2-aminobutyrylsarcosyl-N-methyl-L-leucyl-L-valyl-N-methyl-L-leucyl-L-alanyl-D-alanyl-N-methyl-L-leucyl-N-methyl-L-leucyl-N-methyl-L-valyl-[]]) with excess lithium diisopropylamide followed by excess methyl iodide via published procedures yields cyclo-[[]((2S,3R,[4R]4S)-N,4-dimethyl-4-(methylthiomethyl)-threonyl)-L-2-aminobuytyryl-N-methyl-D-alanyl-N-methyl-L-leucyl-L-valyl-N-methyl-L-leucyl-L-alanyl-D-alanyl-N-methyl-L-leucyl-N-methyl-L-leucyl-N-methyl-L-valyl[]]).

Also, treatment of the same substrate with a variety of oxidants, e.g., sodium metaperiodate or m-chloroperbenzoic acid produces the corresponding sulfoxide or sulfone.

TABLE 1
Representative Compounds $$R^{10}-R^{11}-R^1-R^2-R^3$$
$$R^9\phantom{xxxx}\phantom{xxx}|$$
$$\phantom{xx}R^8-R^7-R^6-R^5-R^4$$

| $R^1$ | $R^2$ | $R^3$ | $R^4$ | $R^5$ | $R^6$ | $R^7$ | $R^8$ | $R^9$ | $R^{10}$ | $R^{11}$ | Compound |
|---|---|---|---|---|---|---|---|---|---|---|---|
| (2S,1R,[4R]4S)—N,4-dimethyl-4-(methyl)-thiomethyl)threonyl (DMT) | L-2-aminobutyryl Abu | sarcosyl (Sar) | N—methyl-L-leucyl (MeLeu) | L-Valyl (Val) | MeLeu | L-alanyl (Ala) | D-alanyl (D-Ala) | MeLeu | MeLeu | N—methyl L-valyl (MeVal) | (1) |
| DMT | norvalyl (norVal) | Sar | MeLeu | Val | MeLeu | Ala | D-Ala | MeLeu | MeLeu | MeVal | (2) |
| (2S,3R,[4R]4S)—N,4-dimethyl-4-(ethyl-thiomethyl)threonyl (DET) | Abu | Sar | MeLeu | Val | MeLeu | Ala | D-Ala | MeLeu | MeLeu | MeVal | (3) |
| (2S,3R,[4R]4S)—N,4-dimethyl-4-(phenyl-thiomethyl)threonyl | Abu | Sar | MeLeu | Val | MeLeu | Ala | D-Ala | MeLeu | MeLeu | MeVal | (4) |
| (2S,3R,[4R]4S)—N,4-dimethyl 4-(isopropyl0 thiomethyl)threonyl | Abu | Sar | MeLeu | Val | MeLeu | Ala | D-Ala | MeLeu | MeLeu | MeVal | (5) |
| (2S,3R,[4R]4S)—N,4-dimethyl-o-fluoro-phenylthiomethyl)threonyl | Abu | Sar | MeLeu | Val | MeLeu | Ala | D-Ala | MeLeu | MeLeu | MeVal | (6) |
| DMT | Abu | N—methyl-D-alanyl (Me—D-Ala) | MeLeu | Val | MeLeu | Ala | D-Ala | MeLeu | MeLeu | MeVal | (7) |
| DMT | L-threonyl (Thr) | Sar | MeLeu | Val | MeLeu | Ala | D-Ala | MeLeu | MeLeu | MeVal | (8) |
| (2S,3R,[4R]4S)—4-allylmethyl)-N,4-dimethyl)threonyl (ADT) | Abu | Sar | MeLeu | Val | MeLeu | Ala | D-Ala | MeLeu | MeLeu | MeVal | (9) |
| DMT | Abu | Sar | MeLeu | Val | NorVal | Ala | D-Ala | MeLeu | MeLeu | MeVal | (10) |
| DMT | Abu | Sar | MeLeu | Val | MeLeu | Ala | D-Ala | MeLeu | L-Leucyl | MeVal | (11) |
| DMT | Abu | Sar | MeLeu | Val | MeLeu | Abu | D-Ala | MeLeu | MeLeu | MeVal | (12) |
| (2S,3R,[4R]4S)—N,4-dimethyl-4-(2-thiazolylthiomethyl)threonyl | Abu | Sar | MeLeu | Val | MeLeu | Ala | D-Ala | MeLeu | MeLeu | MeVal | (13) |
| DMT | Abu | Sar | MeLeu | Val | MeLeu | Ala | D-Ala | MeLeu | MeLeu | Val | (14) |
| DMT | Abu | D-prolyl | MeLeu | Val | MeLeu | Ala | D-Ala | MeLeu | MeLeu | MeVal | (15) |
| (2S,3R,[4R]4S)—(E-2-butenyl)-N,4-dimethylthreonyl (MeBMT) | (2S,3R,[4R]4S)—4-methyl-4-(methylthiomethyl)-threonyl (MMT) | Sar | MeLeu | Val | MeLeu | Ala | D-Ala | MeLeu | MeLeu | MeVal | (16) |
| DMT | MMT | Sar | MeLeu | Val | MeLeu | Ala | D-Ala | MeLeu | MeLeu | MeVal | (17) |
| DMT | Abu | N—methyl-L-alanyl (MLA) | MeLeu | Val | MeLeu | Ala | D-Ala | MeLeu | MeLeu | MeVal | (18) |
| DMT | Abu | Sar | MeLeu a-(methylmercapto) sarcosyl | Val | MeLeu | Ala | Ala | MeLeu | MeLeu | MeVal | (19) |
| DMT | Abu | Sar | MeLeu | Val | MeLeu | Ala | D-Ala | MeLeu | MeLeu | MeVal | (20) |

TABLE 1-continued

Representative Compounds $$R^{10}-R^{11}-R^1-R^2-R^3$$
$$R^9\diagdown \quad \diagup$$
$$R^8-R^7-R^6-R^5-R^4$$

| $R^1$ | $R^2$ | $R^3$ | $R^4$ | $R^5$ | $R^6$ | $R^7$ | $R^8$ | $R^9$ | $R^{10}$ | $R^{11}$ | Compound |
|---|---|---|---|---|---|---|---|---|---|---|---|
| (2S,3R,[4R]4S)—N,4-dimethyl-4-(methyl-sulfinylmethyl)threonyl | Abu | Sar | MeLeu | Val | MeLeu | Ala | D-Ala | MeLeu | MeLeu | MeVal | (21) |
| DMT | L-serinyl | Sar | MeLeu | Val | MeLeu | Ala | D-Ala | MeLeu | MeLeu | MeVal | (22) |
| DMT | Abu | Sar | MeLeu | Val | MeLeu | Ala | D-Ala | MeLeu | MeLeu | MeVal | (23) |
| DMT | Abu | Sar | MeLeu | Val | MeLeu | Ala | D-Ala | MeLeu | MeLeu | Abu | (24) |
| DMT | Abu | Sar | MeLeu | Val | MeLeu | Ala | D-Ala | MeLeu | MeLeu | Abu | (25) |

Starting materials of the process described in Scheme I are mostly known and available commercially except the key starting material, the threonine derivative (1). Generally the threonine derivatives of formula (1) can be prepared by known methods. For example:

(a) amination of an epoxide derived from a suitable unsaturated carboxylic acid derivative (*J. Chem. Soc.* (1962) 1116); (b) condensation of a substituted-thio propionaldehyde with glycine (*Bull. Chem. Soc. Japan* 44 (1979) 3967); (c) condensation of an aldehyde with isonitriles (*Angew. Chem., Int. Ed. Engl.* 13 (1974) 789; (d) preparation from chiral glycine synthon enolates (*J. Am. Chem. Soc.* 108 (1986) 6757); and (e) preparation from diethyl tartrate (*Helv. Chim. Acta* 66 (1983) 2308). Various threonine derivaties as illustrated below in Scheme II were prepared, for the most part, via modifications of procedures described in (e).

injections, intravenous, intramuscular, intrasternal injection or infusion techniques.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The Scheme II

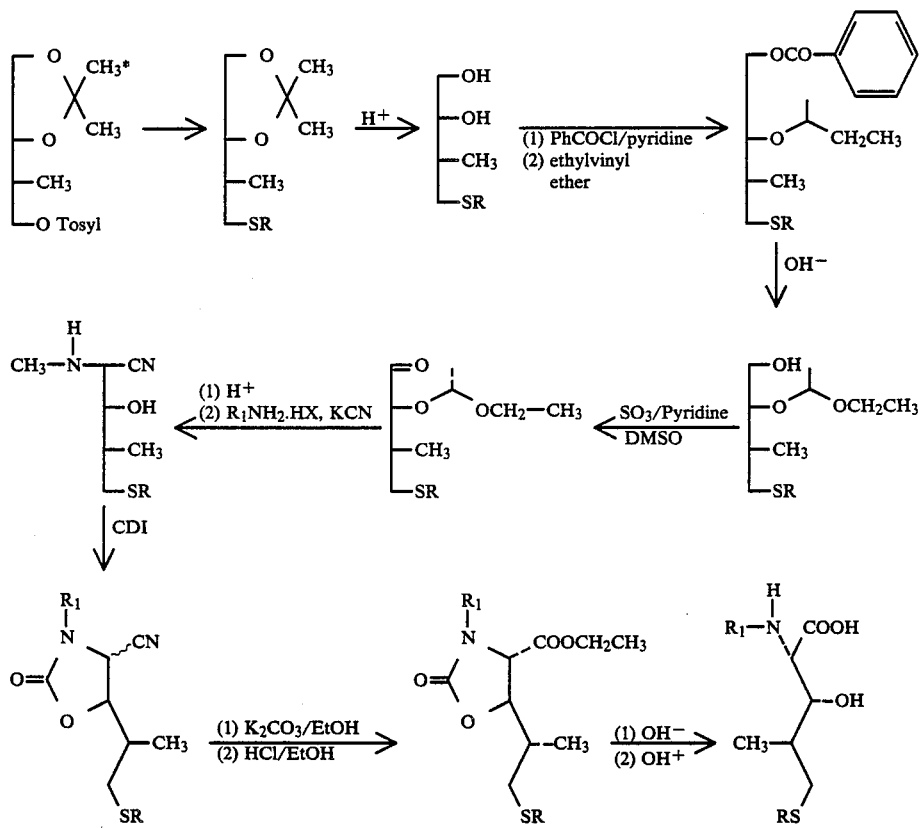

*From Diethyl L(+)-tartrate according to the procedures of R. M. Wenger, Helv. Chim. Acta, 66. 2317 (1983) or Kenji Mori et al., Tetrahedron, 36, 87 (1980).

C. Utility of the compounds within the scope of the invention

This invention also relates to a method of treatment for patients suffering from immunoregulatory abnormalities involving the administration of a compound of formula (I) as the active constituent.

For the treatment of these conditions and diseases caused by immunoirregularity a compound of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous excipients used may be for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat.

Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be (a) a naturally-occurring phosphatide such as lecithin, (b) a condensation product of an alkylene oxide with a fatty acid, for example, polyoxyethylene stearate, (c) a condensation product of ethylene oxide with a long chain aliphatic alcohol, for example, heptadecaethyleneoxycetanol, (d) a condensation product of ethylene oxide with a partial ester derived from a fatty acid and a hexitol such as polyoxyethylene sorbitol monooleate, or (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be prepared by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the immunoregulants are employed.

Dosage levels of the order from about 0.5 mg to about 100 mg per kilogram of body weight per day are useful in the treatment of the above-indicated conditions (from about 25 mg to about 5 gms. per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

D. Biological evidence in support of utility of the compounds within the scope of the invention It has been found that the compounds of formula (I) have immunosuppressive activities and are thereby useful in the treatment of various "autoimmune" and chronic inflammatory diseases. They may also be useful in the prevention of graft rejection or rejection of "donor" organs in transplantation operations. The following table illustrates and supports the utility of the compounds of the present invention:

TABLE 2

CYCLOPHILIN BINDING ASSAY[a]

$$\begin{array}{c}
\text{RS} \\
\text{CH}_3 \\
\text{—OH} \\
\text{CH}_3 \\
\text{MeLeu—MeVal—N} \quad \text{CO—R}^2\text{—Sar} \\
\text{MeLeu} \quad\quad\quad \text{MeLeu} \\
\text{D-Ala——Ala——MeLeu——Val}
\end{array}$$

| Compound | R | $R^2$ | CYCLOPHILIN BINDING (% OF CsA Activity)[b] |
|---|---|---|---|
| (a) | $CH_3$ | Abu | 179 |
| (b) | $CH_3$ | nVal | 58 |
| (c) | $CH_3CH_2$ | Abu | 96 |
| (d) | $CH_3\!\!>\!\!\!<\!\!CH_3$ | Abu | 184 |
| (e) | Phenyl | Abu | 18 |

[a]This assay is described in detail by R. Handschumacher et. al., Science, 226, 554 (1984)
[b]Average of multiple assays

EXAMPLE 1

Preparation of Starting Threonine Derivatives

Step A: Preparation of (2R,[3R]3S)-3,4-Isopropylidene-dioxy-2-methyl-1-(methylthio)-butane (A)

To a stirred, ice-cooled solution of sodium methylmercaptide (from 3.0 g., 0.13 g.atm. of sodium and excess anhydrous methyl mercaptan) in anhydrous methanol (250 ml.) was added dropwise a solution of crude (2R,3R)-3,4-isopropylidene-dioxy-2-methylbutyl p-toluenesulfonate (10.0 g., 0.0318 m) (prepared according to the procedures described by *Helv. Chim. Acta.*, 66 (1983), 2317 or Tetrahedron 36, (1980), 89) in anhydrous ether (50 ml.). The resultant mixture was stirred cold for an additional one hour, and then allowed to stir at ambient termperatures until thin-layer (tlc) analysis indicated the absence of tosylate. Nitrogen gas was used to displace the excess methyl mercaptan, the reaction mixture concentrated in vacuo to a residue, the residue distributed between methylene chloride and water, the aqueous layer re-extracted one time with methylene chloride, and the combined organic layers dried over sodium sulfate. The concentrated residue was then chromatographed on a 300 g. silica gel column using 10% ether in hexane as eluant to yield 3.7 g. (A) as a volatile oil. N.m.r. and Mass spectrum were consistent with the structure, $[\alpha]_D = +15.0°$ (c=1, $CDCl_3$).

Step B: Preparation of (2R, [3R]3S)-3-Methyl-4-(methylthio)-1,2-butanediol (B)

To a stirred solution of (A) (5.6 g., 0.0294 m.) in peroxide free tetrahydrofuran (250 ml.) was added dropwise a solution of dilute HCl (from 17 ml. Fisher 2N HCl diluted to 68 ml. with water). The resultant mixture was evacuated 4 times under a nitrogen atmosphere and allowed to stir at room temperature until tlc analysis (10% ether in hexane) indicated the absence of (A). The pH was adjusted to ca. 7 with fresh saturated sodium hydrogen carbonate solution and the THF removed in vacuo. Repeated extraction of the resulting aqueous layer with methylene chloride yields 3.7 g (84%) of oily (B). N.m.r. spectrum was consistent with the structure; Mass spectrum, $M^+ = 150$; $[\alpha]_D = +14.5°$ (c=0.9, $CDCl_3$).

Step C: Preparation of (2R, [3R]3S)-1-Benzoyloxy-3-methyl-4-(4-methylthio)-2-butanol (C)

To a stirred, ice-cooled solution of (B) (3.7 g., 0.025 m.) in dried pyridine (30 ml.) was added dropwise over ca. 5 minutes under a nitrogen atmosphere a solution of benzoyl chloride (3.0 ml., 0.026 m.) in dry ether (5 ml.). The mixture was stirred for an additional 5 minutes, the ice-bath removed, and the mixture allowed to stir at ambient temperatures. After ca. 1.5 hr., tlc analysis indicated that the reaction was complete and the mixture was transferred to a separatory funnel with ether (300 ml.). The mixture was washed 1X with water (100 ml.), 4X with saturated copper sulfate solution, 1X with saturated sodium chloride solution and dried over sodium sulfate. Concentration of the filtered solution followed by chromatography on silica gel (200 g.; 1% methanol/methylene chloride as eluant) yields 5.4 g (C) as an oil. N.m.r. was consistent with the structure $[\alpha]_D = +9.1$ (c=0.75, $CDCl_3$).

Step D: Preparation of (2R, [3R]3S)-1-Benzoyloxy-2-(1'-ethoxyethoxy)-3-methyl-4-(methylthio)butane (D)

To a stirred solution of (C) (5.4 g., 0.021 m.) in dry methylene chloride (60 ml.) was added ethyl vinyl ether (8 ml., 0.084 m.) followed by one small drop of anhydrous trifluoroacetic acid. The mixture was allowed to stir in a closed container at ambient temperatures until tlc analysis indicated that the reaction was complete. Anhydrous sodium hydrogen carbonate (0.1 g.) was then added, the mixture allowed to stir for ca. one hour, and the volatiles removed in vacuo. The crude (D) was used immediately in the next step.

Step E: Preparation of (2R,[3R]3S)-2-(1'-Ethoxyethoxy)-3-methyl4-(methylthio)-1-butanol (E).

A solution of the crude (D) in cold ethanol (60 ml.) was treated with 10N KOH (12 ml.), and the ice-cooled mixture allowed to gradually warm to room temperature. After ca. 40 minutes, tlc analysis indicated that the reaction was complete. The mixture was diluted with methylene chloride (300 ml.), washed with water (200 ml.), the aqueous layer re-extracted 2X with methylene chloride and the combined organic layers dried (sodium sulfate), filtered, and concentrated to 4.6 g. of (E) which was used in the following step without further purification. Nmr was consistent with the structure $[\alpha]_D = -4.0$ (c=0.8, $CDCl_3$).

Step F: Preparation of (2R,[3R]3S)-2-(1'-Ethoxy-ethoxy)-3-methyl-4-(methylthio)-1-butanal (F)

To a well stirred solution of (F) (4.1 g., 0.0185 m.) in dried DMSO (50 ml.) was added dry triethylamine (17 ml.) and the resulting mixture cooled under a nitrogen atmosphere to ca. 16° C. A solution of sulfur dioxide-pyridine complex (8.84 g., 0.055 m) in dry DMSO (50 ml.) was then added dropwise over ca. 8 minutes while the temperatue was kept below 30° C. The resulting mixture was stirred at ambient temperatures until the tlc analysis indicated complete reaction. The mixture was diluted with ether (200 ml.), the ether layer washed 1X with water (200 ml.), the aqueous layer re-extracted 2X with ether, and the combined ether layers washed 2X with water and 1X with saturated sodium chloride soltuion. The ether solution was then concentrated in vacuo (temperature <23° C.), and the oily residue used immediately in the next step.

Step G: Preparation of (2R,[3R]3S)-2-Hydroxy-3-methyl-4-(methylthio)-1-butanal (G)

A stirred solution of (F) (from above) in fresh THF (75 ml.) was treated with 1N HCl (15 ml.) The mixture was deaerated under a nitrogen atmosphere and stirred at ambient temperatures until tlc analysis indicated no compound (F) remained. The mixture was transferred to a separatory funnel with methylene chloride (300 ml.), washed 1X with water (300 ml.), and the aqueous layer re-extracted 2X with methylene chloride. The organic layers were combined and washed 1X with water and concentrated in vacuo to compound (G) as an oil which was used immediately in the following step.

Step H: Preparation of (2RS,3R,[4R]4S)-3-Hydroxy-4-methyl-2-(methylamino)-5-(methylthio)pentanenitrile (H)

Compound (G) was dissolved in methanol (120 ml.) and the stirred solution treated sequentially with potassium cyanide (1.82 g., 0.028 m), methylamine hydrochloride (2.03 g., 0.03 m.), and water (20 ml.). The sides of the flask were rinsed down with an additional 5 ml of methanol, the mixture covered with a nitrogen atmosphere and allowed to stir overnight at room temperature. The mixture was then concentrated in vacuo to a slurry. This was distributed between methylene chloride (300 ml.) and water (400 ml.), separated, and the aqueous layer re-extracted 2x with methylene chloride. The combined organic layers were dried over sodium sulfate and concentrated to yield compound (H) as a waxy solid (3.1 g.). It was used directly in the next step.

Step I: Preparation of 3-Methyl-5-((1'-methyl2'-(methylthio))ethyl)-2-oxooxazolidine-4-carbonitrile (I).

To a stirred solution of (H) (3.1 g., 0.0165 m.) in dried methylene chloride (120 ml.) at room temperature was added 1,1'-carbonyldiimidazole (5.63 g., 0.0347 m.) and the mixture covered with a nitrogen atmosphere and allowed to stir overnight. After transferring to a separatory funnel with methylene chloride (200 ml.), the resultant solution was washed with water, the aqueous layer re-extracted 2X methylene chloride and the combined organic layers dried over sodium sulfate. Concentration of the dried solution yielded 4.0 g. of an oil which after chromatography (silica gel, 0.5% methanol/methylene chloride as eluant) gave 2.4 g. of compound (I) as an oil which crystallized on standing overnight $[\alpha]_D = +37.5°$ (c=0.6, CDCl$_3$).

Step J: Preparation of Ethyl (4S, 5R)-3-methyl-5-(((1'[R]S)-1'methyl-2'-(methylthio))ethyl)-2-oxooxazolidine-4-carboximidate (J)

To a stirred solution of Compound (I) (0.8 g., 0.0037 m) in 95% ethanol (35 ml.) was added crushed, anhydrous potassium carbonate (1.05 g.). The sides of the flask was rinsed down with an additional 5 ml. of ethanol, and the mixture allowed to stir at room temperature. After 6 hours, the mixture was transferred quickly to a separatory funnel, and methylene chloride (500 ml.) followed by water (150 ml.) was added. The mixture was shaken, separated, the aqueous layer re-extracted 2X with methylene chloride, and the combined organic layer dried over sodium sulfate. Concentration of the dried organic layer yielded 0.85 g of compound (J) (Mass spectrum, M+=214) which was used directly in the next step.

Step K: Preparation of Ethyl (4S, 5R)-3-methyl-5-(((1'[R]S)-1'-methyl-2'-(methylthio))ethyl)-2-oxooxazolidine-4-carboxylate (K)

To a stirred solution of Compound (J) (0.85 g., 0.00327 m.) in 95% ethanol (90 ml.) was immediately added 1N HCL (4.5 ml., 0.0045 m.), and the mixture allowed to stir until tlc analysis indicated no compound (J) remained. The pH of the solution was brought to ca. 7 with 1N sodium hydrogen carbonate solution and the mixture distributed between methylene chloride (300 ml.) and water (150 ml.). The aqueous layer was re-extracted with 100 ml. methylene chloride and the combined organic layers dried over sodium sulfate. Concentration of the dried organic layer in vacuo yielded 0.8 g. compound (K) as an oil. $[\alpha]_D = +33.7°$ (c=0.6, CDCl$_3$); Mass spectrum, M+=261.

Step L: Preparation of (2S, 3r, [4R]4S)-3-Hydroxy-4-methyl-2-(methylamino)-5-(methylthio)pentanoic acid (L)

To a stirred solution of Compound (K) (0.75 g., 0.00287 m) was added aqueous 2N potassium hydroxide (20 ml.). The resultant two phase mixture was evacuated several times under nitrogen, and the mixture heated in an oil-bath to a bath temperature of 87° C. After eleven hours at this temperature the murky solution was allowed to cool, the aqueous solution pipetted through a small plug of glass wool to remove a small amount of dark oily matter, the clear filtrate cooled in an ice bath and the pH of the cold solution brought to ca. 5 with 1N hydrochloric acid. Concentration of the solution yielded 3.7 g. of a compound (L)/KCl mixture which upon chromatography on a Sephadex LH20 column (methanol as eluant) yielded 0.4 g. of crystalline compound (L). $[\alpha]_D = +27.7$ (c=0.3, D$_2$O). Nmr (D$_2$O; H$_2$O ref=4.88 ppm; δ 1.20 (3H, d, 4-CH$_3$); 2.22 (3H, s, SCH$_3$; 2.85 (3H, s, NCH$_3$)

Following essentially the procedures described in Steps A to L, the following threonine derivatives (Table 3) were made as shown below.

For example, when sodium (or potassium) ethylmercaptide was used in place of the sodium methylmercaptide in Step A, one obtained (2S, 3R, 4R)-5-(ethylthio)-3-hydroxy-4-methyl-2-(methylamino)pentanoic acid. Likewise, when the methylamine hydrochloride of Step H was replaced by ammonium chloride, (2S, 3R, [4R]4S)-2-amino-3-hydroxy-4-methyl-5-(methylthio)-pentanoic acid was obtained, and when ethylamine hydrochloride was used, (2A, 3R, [4R]4S)-2-(ethylamino)-3-hydroxy-4-methyl-5-(methyl-thio)pentanoic acid was obtained.

TABLE 3

Representative Threonine Derivates

| Compound | R | $[\delta]_D°$ | (Solvent, C) | M.P. (C) |
|---|---|---|---|---|
| (a) | CH$_3$CH$_2$ | +47 | (D$_2$O, 0.34) | 216.5 dec. |
| (b) | CH$_3$\_/CH$_3$ (isopropyl) | +41 | (D$_2$O, 0.50) | 207 dec. |
| (c) | phenyl | +75 | (D$_2$O, 0.57) (NaOD) | 213 dec. |

EXAMPLE 2

Preparation of Cyclosporins

Following essentially the same procedures described by R. W. Wenger et al. in Helv. Chim. Acta, 2308 (1983) and scheme 1 at page 8, the following representative cyclosporins were prepared (Table 4):

TABLE 4
Representative Thia Cyclic Undecapeptides (Cyclosporins)

```
                          RS
                    CH3    \
          MeLeu—MeVal—(CH3)N   —OH
         /                  \CO—R2
   MeLeu                          MeLeu
         \                        /
         D-Ala——L-Ala—MeLeu——Val
```

| Compound | R | $R^2$ | $[\alpha]_D°$ (CDCl$_3$) (C) | M.P. (C°) | M.S. (M$^+$) (FAB) |
|---|---|---|---|---|---|
| (a) | CH$_3$ | Abu | −224 (0.21) | 134–138 | 1208 |
| (b) | CH$_3$ | nVal | −217 (0.17) | 146–150 | 1222 |
| (c) | CH$_3$CH$_2$ | Abu | −210 (0.17) | 140–145 | 1222 |
| (d) | (CH$_3$)$_2$CH— | Abu | −206 (0.21) | 137–140 | 1236 |
| (e) | phenyl | Abu | −196 (0.21) | 141–144 | 1270 |

What is claimed is:

1. A compound of formula $$R^{10}-R^{11}-R^1-R^2-R^3 \atop R^9 \qquad\qquad\qquad\quad | \atop R^8-R^7-R^6-R^5-R^4} \quad (I)$$

wherein $$R^1 \text{ is } -N-C-(CO)- \text{ with } CH_2XR, CHR_a, R_e, CH(OH)$$

where X, R, R$_a$ and R$_e$ are as defined below;

R is
(1) hydrogen;
(2) loweralkyl;
(3) loweralkenyl;
(4) haloloweralkyl;
(5) aryl;
(6) oxyloweralkyl comprising alkoxy lower alkyl and hydroxy lower alkyl;
(7) thioloweralkyl comprising alkyl thio lower alkyl and mercapto lower alkyl;
(8) heteroaryl;

the aryl or hetoroaryl group can be substituted with one or more functional groups selected from a group consisting of
(a) C$_{1-6}$ alkyl,
(b) C$_{1-6}$ alkanoyl;
(c) C$_{1-6}$ haloalkyl;
(d) halo;
(e) cyano;
(f) hydroxy C$_{1-3}$ alkyl;
(g) C$_{1-6}$ alkoxy;
(h)

$$C_{1-6}\text{alkyl-S}- \atop \downarrow \atop (O)_n$$

where n is 0, 1 or 2;
(i) —NR$_b$COR$_c$ wherein R$_b$ and R$_c$ independently are H or C$_{1-6}$ alkyl;
(j) —NO$_2$;
(k) —NR$_b$R$_c$;
(l) —OR$_b$;
(m) —CONR$_b$R$_c$
(n) —COR$_b$;
(o) —NR$_b$CONR$_b$R$_c$;
(p) —NR$_b$COR$_c$;
(q) —OCOR$_b$;
(r) —SCOR$_b$; or
(s) —OCH$_2$O—; and x is S, SO, SO$_2$, or NR$_6$.
R$_a$ is loweralkyl;
R$_e$ is loweralkyl; loweralkylphenyl; or aryl;
$R^2$ is L-2-aminobutyryl; norvalyl; L-threonyl; or R$^1$;
$R^3$ is sarcosyl; α-(methylmercapto)-sarcosyl; N-methyl-D-alanyl; N-methyl-L-alanyl; or D-prolyl;
$R^4$ is N-methyl-L-leucyl;
$R^5$ is L-valyl; or norvalyl;
$R^6$ is N-methyl-L-leucyl;
$R^7$ is L-analyl; L-2-aminobutyryl; or L-phenylalanyl;
$R^8$ is D-alanyl or L-alanyl;
$R^9$ is N-methyl-L-leucyl; or N-methyl-L-valyl;
$R^{10}$ is N-methyl-L-leucyl; or L-leucyl; and
$R^{11}$ is N-methyl-L-valyl; L-valyl; N-methylleucyl; or L-2-aminobutyryl.

2. The compound of claim 1 wherein
R is
(1) hydrogen;
(2) C$_{1-6}$ alkyl;
(3) —CF$_3$;
(4) phenyl;
R$_a$ is C$_{1-6}$alkyl;
X is S or O; and
R$_e$ is C$_{1-6}$ alkyl.

3. The compound of claim 2 wherein
R is C$_{1-6}$ alkyl or phenyl;
R$_a$ is methyl;
X is S; and
R$_e$ is methyl.

4. A compound according to claim 1, selected from the group consisting of compounds of the formula (I) wherein:
(a) $R^7$ is Ala, $R^8$ is D-Ala, $R^9$ MeLeu, $R^{10}$ is MeLeu, $R^{11}$ is MeVal, and
(1) $R^1$ is DMT, $R^2$ is Abu, $R^3$ is Sar, $R^4$ is MeLeu, $R^5$ is Val, $R^6$ is MeLeu;

(2) $R^1$ is DMT, $R^2$ is NorVal, $R^3$ is Sar, $R^4$ is MeLeu, $R^5$ is Val, $R^6$ is MeLeu;
(3) $R^1$ is DET, $R^2$ is Abu, $R^3$ is Sar, $R^4$ is MeLeu, $R^5$ is Val, $R^6$ is MeLeu;
(4) $R^1$ is (2S, 3R, 4S)-N, -4-dimethyl-4-(phenylthiomethyl)threonyl, $R^2$ is Abu, $R^3$ is Sar, $R^4$ is MeLeu, $R^5$ is Val, $R^6$ is MeLeu;
(5) $R^1$ is (2S, 3R, 4S)-N, 4-dimethyl-4-(isopropylthiomethyl)-threonyl, $R^2$ is Abu, $R^3$ is Sar, $R^4$ is MeLeu, $R^5$ is Val, $R^6$ is MeLeu;
(6) $R^1$ is DMT, $R^2$ is Abu, $R^3$ is Me-D-Ala, $R^4$ is MeLeu, $R^5$ is Val, $R^6$ is MeLeu;
(7) $R^1$ is DMT, $R^2$ is Thr, $R^3$ is Sar, $R^4$ is MeLeu, $R^5$ is Val, $R^6$ is MeLeu;
(8) $R^1$ is ADT, $R^2$ is Abu, $R^3$ is Sar, $R^4$ is MeLeu, $R^5$ is Val, $R^6$ is MeLeu;
(9) $R^1$ is DMT, $R^2$ is Abu, $R^3$ is Sar, $R^4$ is MeLeu, $R^5$ is Val, $R^6$ is NorVal;
(10) $R^1$ is (2S, 3R, 4S)-N, 4-dimethyl-4-(2-thiazolylthiomethyl)-threonyl, $R^2$ is Abu, $R^3$ is Sar, $R^4$ is MeLeu, $R^5$ is Val, $R^6$ is MeLeu;
(11) $R^1$ is DMT, $R^2$ is Abu, $R^3$ is D-prolyl, $R^4$ is MeLeu, $R^5$ is Val, $R^6$ is MeLeu;
(12) $R^1$ is DMT, $R^2$ is MMT, $R^3$ is Sar, $R^4$ is MeLeu, $R^5$ is Val, $R^6$ is MeLeu;
(13) $R^1$ is DMT, $R^2$ is Abu, $R^3$ is MLA, $R^4$ is MeLeu, $R^5$ is Val, $R^6$ is MeLeu;
(14) $R^1$ is DMT, $R^2$ is Abu, $R^3$ is Sar, $R^4$ is α-(methylmercapto)-sarcosyl, $R^5$ is Val, $R^6$ is MeLeu;
(15) $R^1$ is (2S, 3R, 4S)-N, 4-(methylsulfinylmethyl)-threonyl, $R^2$ is Abu, $R^3$ is Sar, $R^4$ is MeLeu, $R^5$ is Val, $R^6$ is MeLeu;
(16) $R^1$ is DMT, $R^2$ is L-serinyl, $R^3$ is Sar, $R^4$ is MeLeu, $R^5$ is Val, $R^6$ is MeLeu;
(17) $R^1$ is DMT, $R^2$ is Abu, $R^3$ is Sar, $R^4$ is MeLeu, $R^5$ is Val, $R^6$ is MeLeu;
(18) $R^1$ is DMT, $R^2$ is Abu, $R^3$ is Sar, $R^4$ is MeLeu, $R^5$ is Val, $R^6$ is MeLeu;
(19) $R^1$ is (2S, 3R, 4S)-N, 4-dimethyl-o-(fluorophenylthiomethyl)-threonyl, $R^2$ is Abu, $R^3$ is Sar, $R^4$ is MeLeu, $R^5$ is Val, $R^6$ is MeLeu;
(b) $R^7$ is Ala, $R^8$ is D-Ala; $R^9$ is MeLeu, $R^{10}$ is Leu, $R^{11}$ is MeVal, and $R^1$ is DMT, $R^2$ is Abu, $R^3$ is Sar, $R^4$ is MeLeu, $R^5$ is Val, $R^6$ is MeLeu;
(c) $R^7$ is Abu, $R^8$ is D-Ala; $R^9$ is MeLeu, $R^{10}$ is MeLeu, $R^{11}$ is MeVal, and $R^1$ is DMT, $R^2$ is Abu, $R^3$ is Sar, $R^4$ is MeLeu, $R^5$ is Val, $R^6$ is MeLeu,
(d) $R^7$ is Ala, $R^8$ is D-Ala; $R^9$ is MeLeu, $R^{10}$ is MeLeu, $R^{11}$ is Val, and $R^1$ is DMT, $R^2$ is Abu, $R^3$ is Sar, $R^4$ is MeLeu, $R^5$ is Val, $R^6$ is MeLeu;
(e) $R^7$ is Ala, $R^8$ is Ala, $R^9$ is MeLeu, $R^{10}$ is MeLeu, $R^{11}$ is MeVal, and $R^1$ is DMT, $R^2$ is Abu, $R^3$ is Sar, $R^4$ is MeLeu, $R^5$ is Val, $R^6$ is MeLeu; or
(f) $R^7$ is Ala, $R^8$ is D-Ala, $R^9$ is MeLeu, $R^{10}$ is MeLeu, $R^{11}$ is Abu, and $R^1$ is DMT, $R^2$ is Abu, $R^3$ is Sar, $R^4$ is MeLeu, $R^5$ is Val, $R^6$ is MeLeu.

5. A pharmaceutical composition for the prevention of immunoregulatory disorders or diseases comprising a pharmaceutical carrier and a therapeutically effective amount of compound of formula (I), according to claim 1.

6. A pharmaceutical compostion for the control of immunoregulatory disorders or diseases comprising a pharmaceutical carrier and a therapeutically effective amount of compound of formula (I), according to claim 1.

7. A pharmaceutical composition for the treatment of immunoregulatory disorders or diseases comprising a pharmaceutical carrier and a therapeutically effective amount of compound of formula (I), according to claim 1.

8. A pharmaceutical composition for the prevention of immunoregulatory disorders or diseases comprising a pharmaceutical carrier and a therapeutically effective amount of compound of formula (I), according to claim 4.

9. A pharmaceutical composition for the control of immunoregulatory disorders or diseases comprising a pharmaceutical carrier and a therapeutically effective amount of compound of formula (I), according to claim 4.

10. A pharmaceutical composition for the treatment of immunoregulatory disorders or diseases comprising a pharmaceutical carrier and a therapeutically effective amount of compound of formula (I), according to claim 4.

11. A method for the prevention of immunoregulatory disorders or diseases compromising the administration to a mammalian species in need of such prevention an effective amount of a compound of formula (I) according to claim 1.

12. A method for the control of immunoregulatory disorders or diseases compromising the administration to a mammalian species in need of such control an effective amount of a compound of formula (I) according to claim 1.

13. A method for the treatment of immunoregulatory disorders or diseases compromising the administration to a mammalian species in need of such treatment an effective amount of a compound of formula (I) according to claim 1.

14. A method for the prevention of immunoregulatory disorders or diseases compromising the administration to a mammalian species in need of such prevention an effective amount of a compound of formula (I) according to claim 4.

15. A method for the control of immunoregulatory disorders or diseases compromising the administration to a mammalian species in need of such control an effective amount of a compound of formula (I) according to claim 4.

16. A method for the treatment of immunoregulatory disorders or diseases compromising the administration to a mammalian species in need of such treatment an effective amount of a compound of formula (I) according to claim 4.

17. A compound of formula

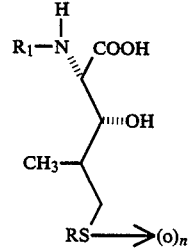

wherein
$R_1$ is H or $C_{1-6}$alkyl;
R is
(1) hydrogen;
(2) loweralkyl;
(3) loweralkenyl;

(4) haloloweralkyl;
(5) aryl;
(6) oxyloweralkyl comprising alkoxy lower alkyl and hydroxy lower alkyl;
(7) thioloweralkyl comprising alkyl thio lower alkyl and mercapto lower alkyl;
(8) heteroaryl;

the aryl or heteroaryl group above can be substituted with one or more functional groups selected from a group consisting of (a) $C_{1-6}$ alkyl,
(b) $C_{1-6}$ alkanoyl;
(c) $C_{1-6}$ haloalkyl;
(d) halo;
(e) cyano;
(f) hydroxy $C_{1-3}$ alkyl;
(g) $C_{1-6}$ alkoxy;
(h)

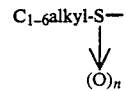

where n is 0, 1 or 2;
(i) —$NR_bCOR_c$ wherein $R_b$ and $R_c$ independently are H or $C_{1-6}$ alkyl;
(j) —$NO_2$;
(k) —$NR_bR_c$;
(l) —$OR_b$;
(m) —$CONR_bR_c$
(n) —$COR_b$;
(o) —$NR_bCONR_bR_c$;
(p) —$NR_bCOR_c$;
(q) —$OCOR_b$;
(r) —$SCOR_b$; or
(s) —$OCH_2O$—; and n is 0, 1 or 2.

18. The compound of claim 17 wherein R is $C_{1-6}$alkyl, phenyl, substituted phenyl, $C_{2-8}$alkenyl, and thiazolyl.

19. The compound of claim 17 wherein R is methyl, ethyl, isopropyl, butenyl, phenyl, O-fluorophenyl, alkyl, 2-thiazolyl.

* * * * *

UNITED STATES PATENT AND TRADEMARK OFFICE
CERTIFICATE OF CORRECTION

PATENT NO. : 4,798,823

DATED : January 17, 1989

INVENTOR(S) : Bruce E. Witzel

Page 1 of 3

It is certified that error appears in the above-identified patent and that said Letters Patent is hereby corrected as shown below:

At column 6, line 55 "[[](((2S,3R,[4R]4S)" should read —-(((2S,3R,4S)—-.

At column 6, line 59 "L-valyl-[]])" should read —-L-valyl-)—-.

At column 6, line 61 "[[]((2S,3R,[4R]4S)" should read —-((2S,3R,4S)—-.

At column 6, line 65 "valyl[]])" should read —-valyl)—-.

In Table I at columns 7 and 8 the stereochemical designation of $R^1$ in compound 1 as "(2S, 1R,[4R]4S)" should read —-(2S,3R,4S)—-.

In Table I at columns 7 and 8 the stereochemical designation of $R^1$ in compound 3 as "(2S,3R,[4R]4S)" should read —-(2S,3R,4S)—-.

In Table I at columns 7 and 8 the stereochemical designation of $R^1$ in compound 4 as "(2S,3R,[4R]4S)" should read —-(2S,3R,4S)—-.

In Table I at columns 7 and 8 the stereochemical designation of $R^1$ in compound 5 as "(2S,3R,[4R]4S)" should read —-(2S,3R,4S)—-.

In Table I at columns 7 and 8 the stereochemical designation of $R^1$ in compound 6 as "(2S,3R,[4R]4S)" should read —-(2S,3R,4S)—-.

In Table I at columns 7 and 8 the stereochemical designation of $R^1$ in compound 9 as "(2S,3R,[4R]4S)" should read —-(2S,3R,4S)—-.

In Table I at columns 7 and 8 the stereochemical designation of $R^1$ in compound 13 as "(2S,3R,[4R]4S)" should read —-(2S,3R,4S)—-.

UNITED STATES PATENT AND TRADEMARK OFFICE
CERTIFICATE OF CORRECTION

PATENT NO. : 4,798,823

DATED : January 17, 1989

INVENTOR(S) : Bruce E. Witzel

It is certified that error appears in the above-identified patent and that said Letters Patent is hereby corrected as shown below:

In Table I at columns 7 and 8 the stereochemical designation of $R^1$ in compound 16 as "(2S,3R,[4R]4S)" should read --(2S,3R,4S)--.

In Table I at columns 7 and 8 the stereochemical designation of $R^2$ in compound 16 as "(2S,3R,[4R]4S)" should read --(2S,3R,4S)--.

In Table I at column 9 the stereochemical designation of compound 21 as "(2S,3R,[4R]4S)" should read --(2S,3R,4S)--.

At column 15, line 31 "(2R,[3R]3S)" should read --2R,3S)--.

At column 15, line 55 "(2R,[3R]3S)" should read --2R,3S)--.

At column 16, line 3 "(2R,[3R]3S)" should read --2R,3S)--.

At column 16, line 22 "(2R,[3R]3S)" should read --2R,3S)--.

At column 16, line 35 "(2R,[3R]3S)" should read --2R,3S)--.

At column 16, line 49 "(2R,[3R]3S)" should read --2R,3S)--.

At column 16, line 67 "(2R,[3R]3S)" should read --2R,3S)--.

At column 17, line 13 "(2RS,3R[4R]4S)" should read --(2S,3R,4S)--.

At column 17, line 47 "(((1'[R]S)" should read --(((1'S)--.

UNITED STATES PATENT AND TRADEMARK OFFICE
CERTIFICATE OF CORRECTION

PATENT NO. : 4,798,823

DATED : January 17, 1989

INVENTOR(S) : Bruce E. Witzel

It is certified that error appears in the above-identified patent and that said Letters Patent is hereby corrected as shown below:

At column 17, line 64 "(((1'[R]S)" should read --(((1'S)--.

At column 18, line 11 "2S,3r,[4R]4S)" should read --(2S,3R,4S)--.

At column 18, line 37 "(2S,3R,4R)" should read --(2S,3R,4S)--.

At column 18, line 43 "(2A, 3R, [4R] 4S)" should read --(2S,3R,4S)--.

Signed and Sealed this

Eighteenth Day of December, 1990

*Attest:*

HARRY F. MANBECK, JR.

*Attesting Officer*  *Commissioner of Patents and Trademarks*